United States Patent [19]

Biseniex et al.

[11] Patent Number: 4,487,932
[45] Date of Patent: Dec. 11, 1984

[54] 2,6-DIMETHYL-3,5-BIS-(1-ADAMANTYLHY-DROXYCARBONYL)-4-(2-DIFLUOROME-THOXYPHENYL)-1,4-DIHYDROPYRIDINE

[75] Inventors: Egils A. Biseniex; Maris M. Veveris; Gunar Y. Dubur; Yanis J. Polis, all of Riga; Yan R. Uldrikis, Elgava; Natalia V. Barmenkova; Agris A. Kimenis, both of Riga, all of U.S.S.R.

[73] Assignee: Institut Organicheskogo Sinteza Akademii Nauk Latviiskoi, Riga, U.S.S.R.

[21] Appl. No.: 486,408

[22] Filed: Apr. 19, 1983

[51] Int. Cl.$^3$ .......................................... C07D 211/90
[52] U.S. Cl. .................................. 546/285; 424/266; 546/321
[58] Field of Search .............................. 546/285, 321

[56] References Cited

PUBLICATIONS

Bossert F., et al: Dihydropyridine, eine neue Gruppe stark wirksamer Coronartherapeutica.-Naturwissenschafter, 1971, Bd.58, H.11, S.578.

Kastron V.V., et al.: 2,6-dimethyl-3,5-dicarbomethoxy-4-/o-difluoromethoxyphenyl/-1,4-dihydropyridine Possessing a Marked Hypotensive Activity and Affecting Functions of Vegetative Nervous System, USSR Author's Certificate Bo. 704610/1979/, Discoveries, Inventions, Industrial Designs, Trademarks, 1979, No. 48, p. 88.

Kastron V. V., et al.: Synthesis and Pharmacological Activity of 4-aryl 1, 4-dihydropyridines, -Chemo--Pharmaceutical J., 1982, vol. 16, No. 11, pp. 1322-1329.

Primary Examiner—Alan L. Rotman
Attorney, Agent, or Firm—Ladas & Parry

[57] ABSTRACT

A compound 2,6-dimethyl-3,5-bis-(1-adamantylhydroxycarbonyl)-4-(2-difluoromethoxyphenyl)-1,4-dihydropyridine of the formula

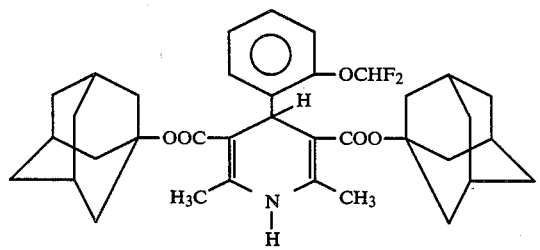

is proposed.

Said compound possesses antianginal activity.

1 Claim, No Drawings

2,6-DIMETHYL-3,5-BIS-(1-ADAMANTYLHYDROX-YCARBONYL)-4-(2-DIFLUOROMETHOXY-PHENYL)-1,4-DIHYDROPYRIDINE

FIELD OF APPLICATION

The present invention relates to a novel chemical compound, and, more particularly, to 2,6-dimethyl-3,5-bis-(1-adamantylhydroxycarbonyl)-4-(2-difluoromethoxyphenyl)-1,4-dihydropyridine possessing an antianginal action and useful in medicine as an active principle of a medicinal preparation.

BACKGROUND OF THE INVENTION

Known in the art is 2,6-dimethyl-4-o-nitrophenyl-3,5-dimethoxycarbonyl-1,4-dihydropyridine(preparation niphedipine) which in its structure and in the spectrum of its pharmacological action is close to the novel compound (cf. W. Vater et al., Arzneimittel-Forsch., 1972, v. 22/1, p.1). Said compound is characterized by a high toxicity, instability when exposed to light, and causes side effects (sharp drop of the blood pressure, tachycardia).

BRIEF DESCRIPTION OF THE INVENTION

It is an object of the present invention to provide a novel compound 2,6-dimethyl-3,5-bis-(1-adamantylhydroxycarbonyl)-4-(2-difluoromethoxyphenyl)-1,4-dihydropyridine possessing an antianginal activity with a wide range of therapeutic action, featuring low toxicity, causing no side effects, and displaying stability in storage.

The compound proposed herein is novel and has not been described in the literature.

According to the invention, 2,6-dimethyl-3,5-bis-(1-adamantylhydroxycarbonyl)-4-(2-difluoromethoxyphenyl)-1,4-dihydropyridine has the following formula

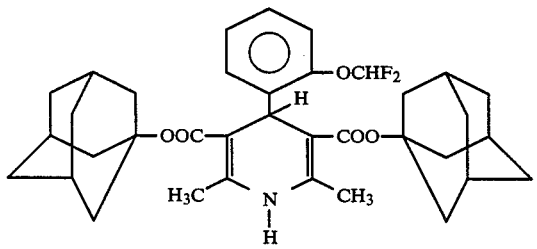

DETAILED DESCRIPTION OF THE INVENTION

The compound of the invention is a light-yellow crystalline powder, readily soluble in ethyl alcohol, chloroform, and other organic solvents and oils. M.p. is 126°–128° C. The compound is stable when stored under conventional conditions.

The biological activity of said compound was studied in experiments with animals.

The action of 2,6-dimethyl-3,5-bis-(1-adamantylhydroxycarbonyl)-4-(2-difluoromethoxyphenyl)-1,4-dihydropyridine on the cardiovascular system was investigated in experiments with cats, rats, and mice. Its specific (antianginal and hypotensive) action and acute toxicity have been studied. For comparison the known hypotensive and antianginal preparation—niphedipine, as well as nitroglycerine, were used.

In experiments with narcotized cats (90 mg/kg of glucochlorose administered intraperitoneally) it has been established that the herein-proposed compound possesses a pronounced coronarodilating action, but is somewhat inferior to niphedipine in activity. Nevertheless, its action in equiactive doses is twice as durative. Unlike niphedipine, the present compound has a positive effect on the coronary circulation in a large range of doses (0.05 to 3 mg/kg) causing no undesirable effects: sharp drop of the arterial pressure, pronounced diminishing of the arterial blood flow, or an increase of the systemic venous pressure.

The results of the investigation are presented in Table 1 hereinbelow.

The present preparation in the range of doses of 0.005 to 3 mg/kg does not cause sharp drop of the arterial pressure, noticeable increase of the systemic venous pressure, or diminution of the aortal blood flow. Meanwhile, niphedipine already in doses exceeding 0.02 mg/kg causes a sharp drop of the arterial pressure (40% of the initial one and over), an increase of the systemic venous pressure, and a pronounced diminution of the aortal blood flow.

Investigations carried out with a view to checking the antianginal action of the present compound have shown that in the range of doses from 0.2 to 3 mg/kg in the experiments with cats it increases the content of oxygen in venous blood outflowing from the coronary sinus of the heart.

In experiments with cats and dogs it has been established that preliminary intravenous administration of the present compound in doses of 0.3 to 2 mg/kg considerably diminishes, and in some cases even completely precludes a rise of the ST segment on the epicardiac leads of the ECG from the focus of ischemia in partial occlusion of the coronary artery and simultaneous superposition of a high artificial rhythm to the heart. The effect of administering the present compound is almost two times more durative and more pronounced than of nitroglycerine in the dose of 0.05 mg/kg. Intravenous administration of niphedipine in doses of 0.01 to 0.05 mg/kg resulted only in an insignificant prevention of the rise of the ST segment during superposition of a high artificial rhythm to the heart in partial occlusion of the coronary artery.

Preliminary administration of the present compound in doses of 0.5 to 2 mg/kg, in contrast to niphedipine, considerably diminished the ischemic change in the heart of dogs in the case oc complete occlusion of the coronary artery.

In experiments with spontaneously hypertensive rats, 1 hour after the peroral administration of the present compound in the dose of 10 mg/kg, lowering of the systolic arterial pressure is 31.5 mm Hg. This is less than after the administration of niphedipine (51.7 mm Hg), but the present compound does not cause tachycardia. In 5 hours lowering of the arterial pressure was for the present compound, 8.6 mm Hg and for niphedipine, 14 mm Hg.

The application of the present compound with daily peroral administration to rats of the line SHR in the dose of 20 mg/kg during 10 days causes lowering of the arterial pressure by 30–60 mm Hg during 24 hours. No increase of the pulse frequency was observed. After the administration of the present compound was discontinued, the systolic arterial pressure gradually rose and reached the control group value in 3 days.

In experiments with white mice it was found that peroral administration of the present compound in doses of 1 to 5 mg/kg prevents the appearance of arrhythmia and cardiac arrest, caused by intravenous administration of calcium chloride. Compared with novocainamide (procainamide) and quinidine, the present compound prevents the appearance of arrhythmia and death of the animal (due to cardiac arest) after administration in smaller doses, and in a more pronounced manner.

In experiments with albino rats, where an aconitic model of arrhythmia was used, the present compound was found to exhibit considerable prophylactic and therapeutic activity (peroral and intravenous administration).

Preliminary peroral administration of the present compound to rabbits in doses of 2 to 10 mg/kg shortens by as much as 2-5 times and considerably alleviates arrhythmia caused by barium chloride (4 mg/kg administered intravenously).

The studies of acute toxicity established the present compound to be low-toxic. $LD_{50}$ of the present compound in intraperitoneal administration is 8400(6885.2–10248) mg/kg. The present compound is considerably less toxic than niphedipine ($LD_{50}$=190 mg/kg), papaverine ($LD_{50}$=91 mg/kg), quinidine ($LD_{50}$=156 mg/kg), and novocainamide (procainamide) ($LD_{50}$=290 mg/kg). The results of studying the acute toxicity are presented in Table 2.

TABLE 1

Results of studying the pharmacological action of 2,6-dimethyl-3,5-bis-(1-adamantylhydroxycarbonyl)-4-(2-difluoromethoxyphenyl)-1,4-dihydropyridine

| Compound | Dose, mg/kg | Increase of space velocity of coronary blood flow % | Duration min | Lowering of arterial pressure, % | Change of systemic venous pressure, % | Change of aortal blood flow, % |
|---|---|---|---|---|---|---|
| Present compound | 0.05 | 10 | 25 | 0 | ±0 | +5 |
|  | 0.50 | 60 | 50 | 5 | −10 | +12 |
|  | 2.00 | 120 | 90 | 20 | +8 | +20 |
| Niphedipine | 0.005 | 12 | 12 | 12 | ±0 | 5 |
|  | 0.02 | 70 | 22 | 35 | +5 | −5−+15 |
|  | 0.06 | 130 | 45 | 60 | +60 | −40−−60 |

TABLE 2

Acute toxicity of investigated compounds for white mice upon intraperitoneal administration

| Preparation | $LD_{50}$, mg/kg | Relative toxicity |
|---|---|---|
| Present compound | 8400(6885.2–10248) | 1 |
| Niphedipine | 190(146.15–247) | 44.2 |
| Papaverine | 91(82–100) | 92.3 |
| Quinidine | 156(111.4–218.4) | 53.8 |
| Novocainamide (procainamide) | 290(145–580) | 28.9 |

As a result of the investigations it is established that:

1. The present compound in doses of 0.1 to 2.0 mg/kg increases the space velocity of the coronary blood flow by 20 to 120% for a period from 30 to 90 min.

2. Alongside of a considerable increase of the space velocity of the coronary blood flow, the present compound in doses of 0.2 to 3 mg/kg increases the content of oxygen in the venous blood outflowing from the coronary sinus of the heart (experiments with cats). The minute volume of the heart somewhat increases. This is an indication, that under the influence of the present compound the work of the myocardium proceeds more economically.

3. The present compound produces a positive effect on the coronary circulation within a wider range of doses (from 0.05 to 3 mg/kg) than niphedipine (from 0.003 to 0.02 mg/kg) without causing such undesirable effects as sharp drop of the arterial pressure or pronounced diminishing of the aortal blood flow.

4. In contrast to niphedipine, the present compound even in large doses upon intravenous administration does not bring about rising of the systemic venous pressure, i.e. it does not cause disorders in the systemic circulation.

5. The action of the present compound in equiactive doses is twice as durative as that of niphedipine.

6. ECG data (epicardium lead) indicate that the present compound is more effective than niphedipine and nitroglycerine, it diminishes myocardial ischemia in both complete occlusion of the coronary artery and in partial occlusion of the coronary artery and simultaneous superposition of high artificial rhythm on the heart (experiments with cats and dogs).

7. Upon peroral administration of the present compound in large doses (10 mg/kg), the arterial pressure in spontaneously hypertensive rats (line SHR) lowers, but the action of the compound is less pronounced than the action of niphedipine. In contrast to niphedipine, the present compound causes no such side effect as tachycardia.

8. The present compound displays antiarrhythmic activity. In experiments with calcium model of arrhythmia the activity of said compound exceeds that of novocainamide (procainamide) and quinidine. The preparation produces a prophylactic and therapeutic effect on aconitic arrhythmia in rats and on barium arrhythmia in rabbits.

9. The present compound has a low toxicity. In experiments with white mice the $LD_{50}$ of the present compound upon intraperitoneal administration is 8400(6885.2–10248) mg/kg. The toxicity of the present compound is 1/44 that of niphedipine ($LD_{50}$ of niphedipine being 190 mg/kg), 1/53 that of quinidine, and 1/28.9 that of novocainamide (procainamide).

The present compound is produced according to the following scheme

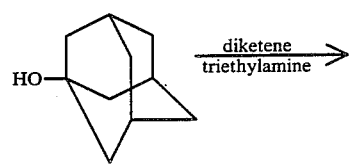

(I)

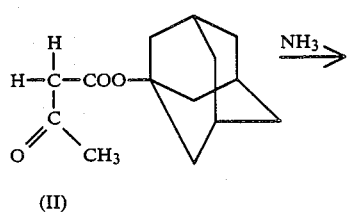

(II)

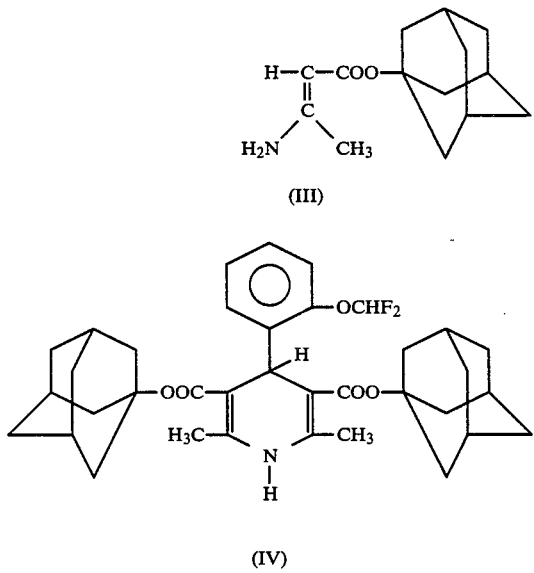

1-Hydroxyadamantane (I) is treated in an inert organic solvent preferably at a temperature of 80° to 100° C. with diketine in the presence of a catalyst, preferably triethylamine. Diketene is added at such a rate that weak boiling of the reaction mixture should be maintained. After adding the total quantity of the diketene, the reaction mixture is heated for another 2 hours to completion of the reaction. Then the organic solvent is distilled off, and the remaining oil is distilled in vacuum. This gives 1-adamantyl ester of acetoacetic acid (II), which is used further for obtaining the desired product.

1-Adamantyl ester of acetoacetic acid (II), 2-difluoromethoxybenzaldehyde and ammonia are subjected to condensation in an organic solvent (ethanol, methanol, dioxane, and the like) preferably at a temperature of 75° to 100° C. for 4 to 10 hours. After cooling of the reaction mixture, the desired product (IV) crystallized during 0.5 to 2 days. The technical-grade product is purified by crystallization from an organic solvent (ethanol, methanol, isopropanol, dioxane, benzene, ethanol-water, and the like).

The present compound can be produced in a different manner as well.

First, as in the above-described embodiment, 1-hydroxyadamantane is treated with diketene, but after distilling-off the solvent, no vacuum distillation is performed; instead, the remaining oil-like product is dissolved in an organic solvent (ethanol, methanol, dioxane, acetone, and the like), and the solution is purged with gaseous ammonia during 0.5 to 2 hours at a temperature of 10° to 50° C. For complete isolation of 1-adamantyl ester of β-aminocrotonic acid (III) the reaction mixture is placed into a cooler for several hours and some quantity of water is added. The precipitate is filtered, washed on the filter with 50% ethanol or methanol, and recrystallized from a mixture of ethanol and water (2:1). The yield of the 1-adamantyl ester of β-aminocrotonic acid (III) is 75–95%. Then condensation of the 1-adamantyl ester of β-aminocrotonic acid and 2-difluoromethoxybenzaldehyde in an organic solvent (ethanol, methanol, dioxane, acetic acid, and the like) is carried out at 75° to 100° C. for 4–10 hours. After cooling the reaction mixture, the desired product is crystallized during 0.5–2 days. Technical-grade product is purified by crystallization from an organic solvent (ethanol, methanol, isopropanol, dioxane, benzene, ethanol-water, and the like).

For a better understanding of the present invention, the following examples of producing the novel compound are given below by way of illustration.

Example 1

16.4 g (1.08 mole) of 1-hydroxyadamantane are dissolved in 200 ml of benzene, heated to the boiling point of the solvent, then 3.0 g (0.03 mole) of triethylamine are added, and, while boiling during an hour, 8.8 g (0.108 mole) of diketene are added gradually, care being taken to avoid overheating. On completion of adding the diketene, the reaction mixture is boiled for another 2 hours. After that benzene and triethylamine are distilled off, and the residue is distilled in a vacuum, to give 16.4 g (64%) of an oily liquid, b.p. 118°–119° C. at 1.5 mm Hg.

Found, %: C 70.9; H 8.7: $C_{14}H_{20}O_3$. Calculated, %: C 71.2; H 8.5

PMR spectrum in $CCl_4$, δ: 1.66 (s, 6H, δ-H of adamantane radical), 1.87 (s, 0.8H of enol), 2.13 (s, 6H, β-H of adamantane radical), 2.17 (s, 6H, $CH_3$ of keto-form and γ-H of adamantyl radical), 3.23 (1.75H of $CH_2$-keto-form), 4.79 ppm (s, 0.25 of CH-enol).

Infrared spectrum (of liquid): 1735 cm$^{-1}$ (C=O)

16.4 g (0.07 mole) of 1-adamantyl ester of acetoacetic acid, 5.4 g (0.035 mole) of o-difluoromethoxybenzaldehyde, and 7.0 g (0.1 mole) of 25% aqueous ammonia are dissolved in 25 ml of ethanol and boiled for 6 hours. After cooling, 9.3 g (45%) of a light-yellow crystalline substance are isolated. M.p. 126°–128° C. (from ethanol).

Found, %: C 70.8; H 7.2; N 2.2: $C_{36}H_{43}NO_5F_2$ Calculated, %: C 71.15; H 7.13 N 2.3

PMR spectrum in $CDCl_3$, δ: 1.60 (s, 12H, δ-H of adamantyl radical), 1.97–2.08 (m, 18H, β-H and γ-H of adamantyl radical), 2.18 (s, 6H, 2.6 —$CH_3$), 5.07 (s, 1H, 4-H), 5.63 (s, 1H, NH), 6.39 (t, 1H, J=78 Hz, $OCHF_2$), 6.95–7.38 ppm (m, 4H, —$C_6H_4$—).

UV spectrum in ethanol, $\lambda_{max}$ (log ε): 207 (4.16), 238 (4.24), and 366 nm (3.82).

Example 2

17.8 g (0.12 mole) of 1-hydroxyadamantane are dissolved in 200 ml of benzene, heated to the boiling point of the solvent, 3 g (0.03 mole) of triethylamine are added, and, while boiling the mixture for about 1 hour, 9.4 g (0.12 mole) of diketene are gradually added to the solution, care being taken to avoid vigorous course of the reaction. On completion of adding the diketene, the mixture is boiled for another 2 hours. After that benzene and triethylamine are distilled off in a vacuum, to give 25 g of an oily liquid—adamantyl ester of acetoacetic acid, which is dissolved without purification in 70 ml of ethanol. Further gaseous ammonia is passed through the solution for 1 hour. Precipitation commences in 30 minutes. For complete separation of the desired product, 15 ml of water are added to the reaction mixture, and the resulting composition is kept in a cooler for several hours. The precipitate is filtered off, washed with 50% ethanol, and dried at room temperature. The procedure gives 23.5 g (85%) of a colourless crystalline substance, m.p. 108°–109° C. (from a mixture of ethanol and water 2:1).

Found, %: C 71.5; H 8.7; N 5.7: $C_{14}H_{21}NO_2$ Calculated, %: C 71.5; H 9.0; N 6.0

PMR spectrum in $CCl_4$, δ: 1.66 (s, 6H, δ-H of adamantane radical), 1.82 (s, 3H, $CH_3$), 2.12 (s, 9H, β-H and γ-H of adamantane radical), 2.77 (br.s, 0.2H NH of imino group), 3.69 (s, 0.4H $CH_2$ of imino form), 4.33 (s, 0.8H, CH of enamine), 5.00–8.00 ppm band, $NH_2$).

Infrared spectrum in Nujol: 1645 and 1740 $cm^{-1}$ (C=O); 3315 and 3440 $cm^{-1}$ (NH).

23.5 g (0.1 mole) of 1-adamantyl ester of β-aminocrotonic acid and 8.6 g (0.05 mole) of o-difluoromethoxybenzaldehyde are dissolved in 50 ml of ethanol and boiled for 7 hours. After cooling the solution is allowed to stand for 1 day, the precipitate is filtered and dried at room temperature. The procedure gives 15.2 g (50%) of a light-yellow crystalline substance. M.p. 126°–128° C. (from ethanol).

Found, %: C 70.8; H 7.2; N 2.2: $C_{36}H_{43}NO_5F_2$ Calculated, %: C 71.15, H 7.13; N 2.3

PMR spectrum in $CDCl_3$, δ: 1.60 (s, 12H, δ-H of adamantyl radical), 1.97–2.08 (m, 18H, β-H and δ-H of adamantyl radical), 2.18 (s, 6H, 2,6-$CH_3$), 5.07 (s, 1H, 4-H), 5.63 (s, 1H, NH), 6.39 (t, 1H, J=78 Hz, $OCHF_2$), 6.95–7.38 ppm (m, 4H, —$C_6H_4$—).

UV spectrum in ethanol, $\lambda_{max}$ (log ε): 207 (4.16), 238 (4.24), and 366 nm (3.82).

What is claimed is:

1. 2,6-Dimethyl-3,5-bis-(1-adamantylhydroxycarbonyl)-4-(2-difluoromethoxyphenyl)-1,4-dihydropyridine of the formula

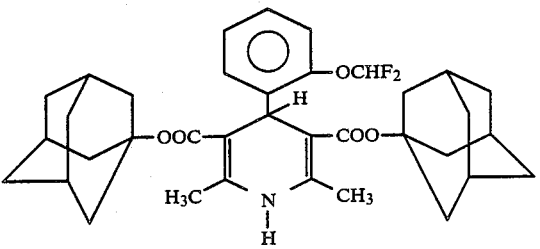

* * * * *